US011253466B2

(12) United States Patent
Forget

(10) Patent No.: US 11,253,466 B2
(45) Date of Patent: Feb. 22, 2022

(54) TOPICAL COMPOSITION FOR REJUVENATING AND/OR REPAIRING SKIN, METHODS, USES AND KITS THEREOF

(71) Applicant: DAVINCIA INC., St-Jérôme (CA)

(72) Inventor: Nathalie Forget, Quebec (CA)

(73) Assignee: DAVINCIA INC., St-Jérôme (CA)

( * ) Notice: Subject to any disclaimer, the term of this patent is extended or adjusted under 35 U.S.C. 154(b) by 14 days.

(21) Appl. No.: 16/634,514

(22) PCT Filed: Jul. 27, 2018

(86) PCT No.: PCT/CA2018/050916
§ 371 (c)(1),
(2) Date: Jan. 27, 2020

(87) PCT Pub. No.: WO2019/018944
PCT Pub. Date: Jan. 31, 2019

(65) Prior Publication Data
US 2021/0113454 A1    Apr. 22, 2021

Related U.S. Application Data

(60) Provisional application No. 62/538,346, filed on Jul. 28, 2017.

(51) Int. Cl.
| | |
|---|---|
| *A61K 8/04* | (2006.01) |
| *A61K 8/9728* | (2017.01) |
| *A61K 8/02* | (2006.01) |
| *A61K 8/66* | (2006.01) |
| *A61K 8/73* | (2006.01) |
| *A61K 8/99* | (2017.01) |
| *A61Q 19/00* | (2006.01) |

(52) U.S. Cl.
CPC .......... *A61K 8/9728* (2017.08); *A61K 8/0212* (2013.01); *A61K 8/04* (2013.01); *A61K 8/66* (2013.01); *A61K 8/735* (2013.01); *A61K 8/99* (2013.01); *A61Q 19/00* (2013.01); *A61K 2800/85* (2013.01)

(58) Field of Classification Search
CPC .................................................. A61K 8/9728
See application file for complete search history.

(56) References Cited

U.S. PATENT DOCUMENTS

2003/0003107 A1 *   1/2003   Farmer .................. A61K 8/925
424/184.1

FOREIGN PATENT DOCUMENTS

| CN | 104586737 A | 5/2015 |
|---|---|---|
| CN | 106333921 A | 1/2017 |

OTHER PUBLICATIONS

International Searching Authority. International Search Report and Written Opinion for application PCT/CA2018/050916, dated Oct. 31, 2018. 11 pages.

(Continued)

*Primary Examiner* — Benjamin J Packard
(74) *Attorney, Agent, or Firm* — Quarles & Brady LLP

(57) ABSTRACT

The present description relates to a skin ointment or topical composition for skin rejuvenation and/or repair. The composition generally comprises: a biocompatible mixture of probiotics (e.g., probiotic yeast and/or bacteria); admixed with one or more of: exfoliating agents, mud and/or clay, blood circulation promoting agent, and nutrients. Methods, uses and kits relating to same are also described.

20 Claims, 11 Drawing Sheets

(56) References Cited

OTHER PUBLICATIONS

Lew, L-C., et al. "Bioactives from probiotics for dermal health: functions and benefits." Journal of Applied Microbiology 114.5 (2013): 1241-1253.
Yahoo Beauty, "Yeast: The Surprisingly Beneficial New Skin Care Ingredient". Yahoo! Lifestyle, Aug. 3, 2015, [online]. Version retrieved from the Internet on Feb. 16, 2018: http://web.archive.org/web/20180216003106/https://www.yahoo.com/lifestyle/yeast-the-surprisingly-beneficial-new-skin-care-125729261908.html.

* cited by examiner

Fig. 1A
Fig. 1B
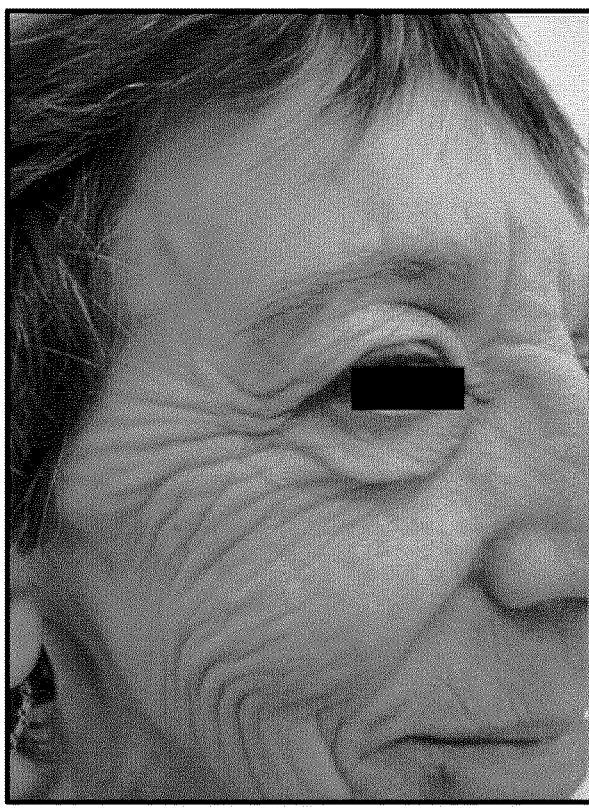 

Fig. 2A
Fig. 2B
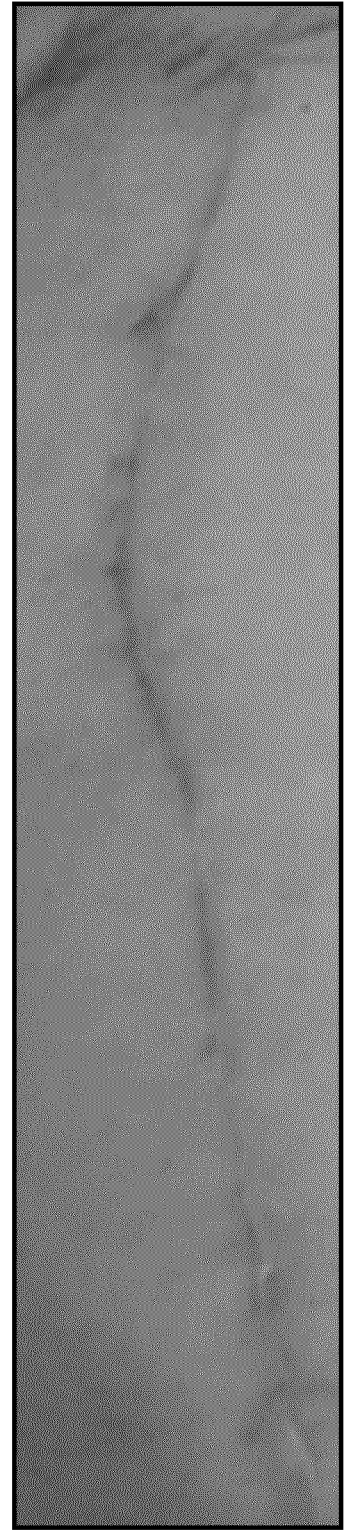

Fig. 4A
Fig. 4B

Fig. 5A
Fig. 5B

Fig. 6A
Fig. 6B
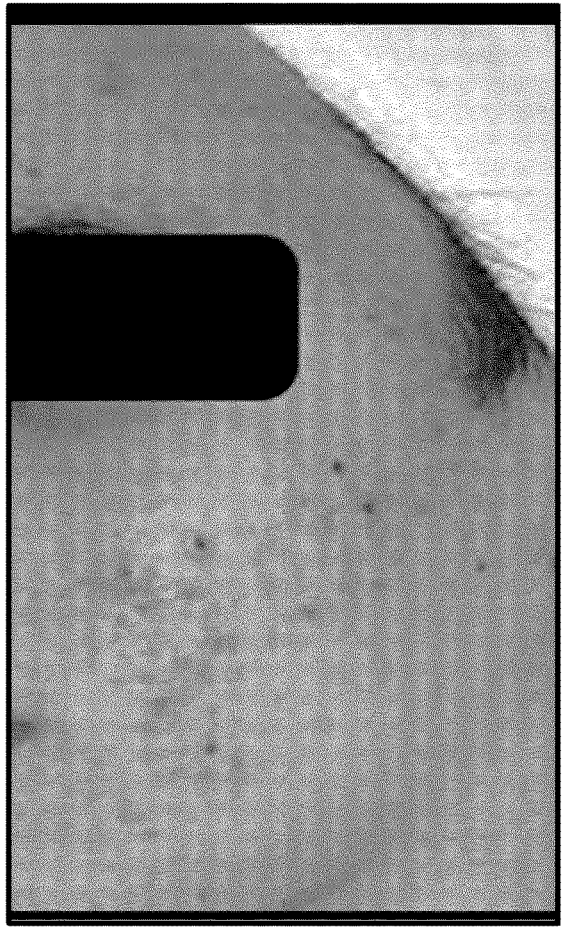
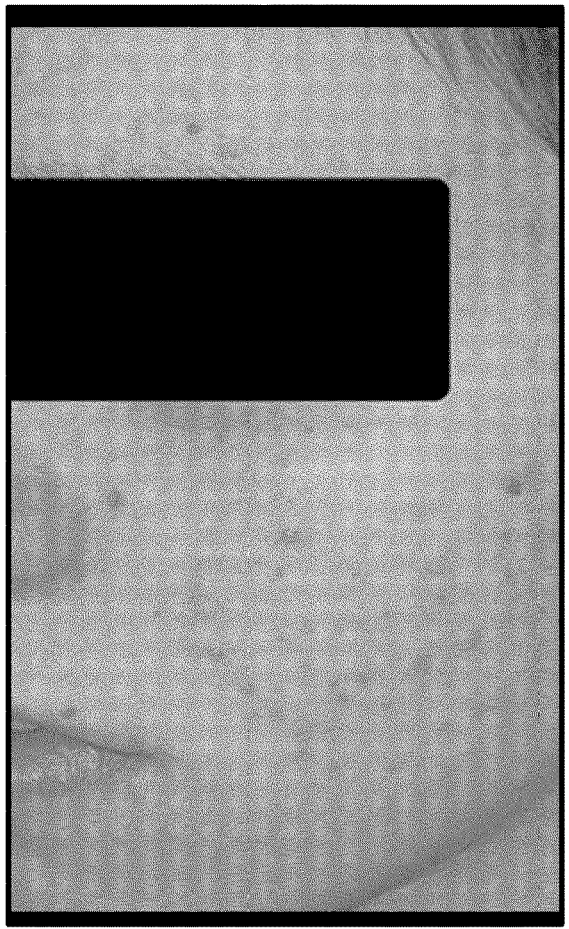

Fig. 7A
Fig. 7B
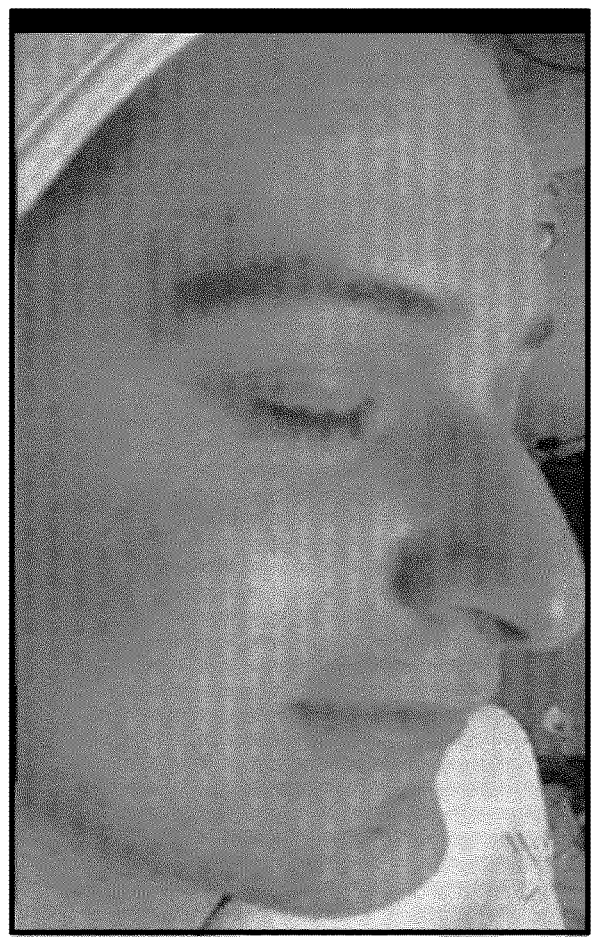

Fig. 8A
Fig. 8B
 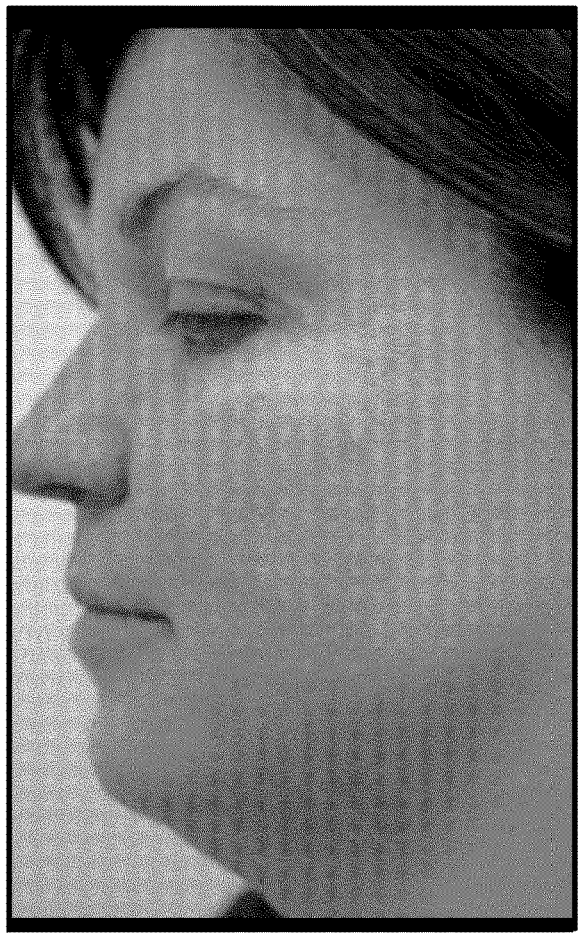

Fig. 9A
Fig. 9B

BEFORE TREATMENT

AFTER TREATMENT

SELECTED REGION
BEFORE TREATMENT

SELECTED REGION
AFTER TREATMENT

BITMAP IMAGE
BEFORE TREATMENT

BITMAP IMAGE
AFTER TREATMENT

TOPICAL COMPOSITION FOR REJUVENATING AND/OR REPAIRING SKIN, METHODS, USES AND KITS THEREOF

The present description relates to topical compositions for treating skin. More specifically, the present description relates topical compositions for rejuvenating and/or repairing skin, methods, uses and kits thereof.

BACKGROUND

Skin care has been practiced for thousands of years and countless dermatological care products/methods are commercially available for beautifying the skin and combating the formation of wrinkles. Some products/methods such as laser techniques, infrared light, or chemical compounds are used to exfoliate and encourage the skin to regenerate new cells.

The effectiveness of skin care products is normally subject to the delivery of active ingredients through the stratum corneum and in the structure of the skin layer of the dermis. Indeed, the active ingredients in the skin care product cannot be effective unless they penetrate through the dead layers of skin tissue and into the layer of living cells of the dermis. While dissolving dead skin layers is an asset, many current products/methods involve aggressive approaches such as using radiation or by application of harsh acids, which destroy this dead skin while debilitating the living cells of the dermis, thus decreasing the potential benefits. Thus, improved skin care products and methods that penetrate through dead skin, and promote skin rejuvenation and/or repair are highly desirable. Also, highly desirable are multifaceted treatments in which a plurality of active ingredients working in concert can be applied in a single treatment.

SUMMARY

The present description relates to topical compositions that promote improved skin rejuvenation and/or repair through the concerted action of active ingredients, including viable probiotic microorganisms. In some embodiments, improved skin rejuvenation and/or repair may include one or more of anti-acne treatment, anti-skin redness treatment, anti-scar treatment, anti-wrinkle treatment, or any combination thereof.

In some aspects, described herein is a skin ointment or topical composition comprising viable probiotic yeast cells and/or viable probiotic bacterial cells; exfoliating agents; a hyperemic (blood circulation promoting) agent; nutrients/prebiotics. The active ingredients, particularly the microorganisms, in the ointments or topical composition described herein are believed to act in concert with the active participation of the skin of the subject to stimulate rejuvenation and/or repair.

In some embodiments, the viable probiotic yeast cells may comprise a *Saccharomyces* yeast (e.g., *Saccharomyces cerevisiae* and/or *Saccharomyces boulardii*), and the viable probiotic bacterial cells may comprise a *Lactobacillus* (e.g., *Lactobacillus acidophilus*, *Lactobacillus rhamnosus*, and/or *Lactobacillus bifidus*).

Other agents found to potentiate the activity of the probiotic microorganisms in the context of the ointments or topical compositions described herein include one or more of proteolytic enzymes, organic acids, cosmetic or dermatologically suitable mud and/or clay, blood circulation promoting agents, nutrients/prebiotics, sugars and/or polysaccharides.

In some embodiments, at least some of the active ingredients of the ointments or topical composition described herein may be formulated in dry form (e.g. and provided in a kit) to improve shelf life, with the dry formulations(s) being combined with an aqueous phase just prior to patient treatment.

General Definitions

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

The use of the word "a" or "an" when used in conjunction with the term "comprising" in the claims and/or the specification may mean "one" but it is also consistent with the meaning of "one or more", "at least one", and "one or more than one".

The term "about" is used to indicate that a value includes the standard deviation of error for the device or method being employed to determine the value. In general, the terminology "about" is meant to designate a possible variation of up to 10%. Therefore, a variation of 1, 2, 3, 4, 5, 6, 7, 8, 9 and 10% of a value is included in the term "about". Unless indicated otherwise, use of the term "about" before a range applies to both ends of the range.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

Other objects, advantages and features of the present description will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 1 shows pictures of a subject before (FIG. 1A) and after (FIG. 1B) receiving treatment with a topical composition of the present description. In this case, the treatment was to improve the appearance of wrinkles, and the picture in (FIG. 1B) shows the result in obtained after five peeling treatments.

FIG. 2 shows pictures of a subject before (FIG. 2A) and after (FIG. 2B) receiving treatment with a topical composition of the present description. In this case, the treatment was for skin scar reduction, and the picture in (FIG. 2B) shows the result obtained after five treatments.

FIG. 4 shows before (A) and after (B) pictures of a patient treated for facial skin tone after 3 biocompatible mask treatments.

FIG. 5 shows before (A) and after (B) pictures of a patient treated for facial acne after 5 biocompatible mask treatments.

FIG. 6 shows before (A) and after (B) pictures of a patient treated for facial acne after 4 biocompatible mask treatments.

FIG. 7 shows before (A) and after (B) pictures of a patient treated for facial acne after 4 biocompatible mask treatments.

FIG. 8 shows before (A) and after (B) pictures of a patient treated for facial rosacea and melasma after 10 biocompatible mask treatments.

FIG. 9 shows before (A) and after (B) pictures of a patient treated for wrinkles after 1 biocompatible mask treatment.

DETAILED DESCRIPTION

Figure 3A:
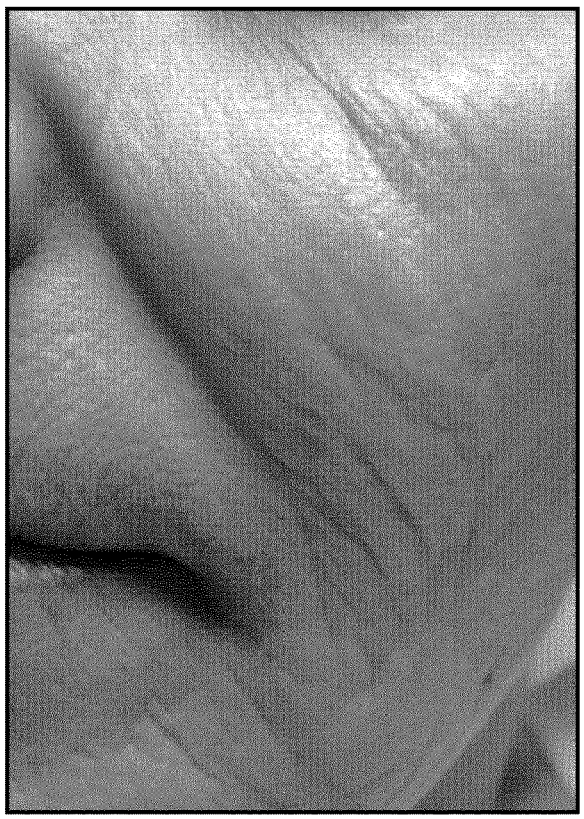
FIG. 3 shows pictures of a subject before (FIG. 3A) and after (FIG. 3B) receiving treatment with a topical composition of the present description. In this case, the treatment was for the reduction of wrinkles and acne scars, and the picture in (FIG. 3B) shows the result obtained after one treatment.

In some aspects, the present description relates to topical compositions that promote improved skin rejuvenation and/or repair through the concerted action of active ingredients. In some embodiments, improved skin rejuvenation and/or repair may include one or more of anti-acne treatment, anti-skin redness treatment, anti-scar treatment, anti-wrinkle treatment, anti-melasma treatment, anti-rosacea treatment, treatment for eye dark circles, treatment for eye puffiness, or any combination thereof.

In some embodiments, the composition may comprise viable probiotic yeast cells, exfoliating agents, and a blood circulation promoting agent.

As used herein, the term "probiotic" refers to a live microorganism (including bacteria or yeast, for example) which, when topically applied in sufficient numbers, beneficially affects the host organism, i.e. by conferring one or more demonstrable health benefits on the host organism. Probiotics are considered beneficial microbiota for organic immunity. Without being bound by theory, their proliferation and/or release of chemical signals/metabolites (e.g., lactic acid) are thought to prevent the proliferation of pathogens.

In some embodiments, the compositions described herein may comprise probiotic yeast cells, such as *Saccharomyces* yeast cells (e.g., *Saccharomyces cerevisiae* and/or *Saccharomyces boulardii*). The yeast cells may comprise selenium yeast or selenium activated fattened yeast. Such yeast may be produced by fermenting the yeast cells in a selenium-rich media, which leads to uptake of selenium by the yeast and integration into yeast proteins (e.g., in selenomethionine). In some embodiments, the yeast may be *Saccharomyces cerevisiae*. Without being bound by theory, the probiotic yeast within the context of topical compositions of the present description may provide harmonization and support to skin cells and skin bacteria. For example, yeast have a hydrolipidic cell membrane similar to that of human cells that have the ability to stick and wrap, then offer their intracellular content upon lysis (e.g., by osmotic transfers). In some embodiments, the probiotic yeast may be present at a concentration of at least 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, or 13% w/w. In some embodiments, the probiotic yeast may be present at a concentration of about 5-14% w/w (e.g., from 5%, 5.5%, 6%, 6.5%, 7%, 7.5%, 8%, 8.5% to 9%, 9.5%, 10%, 10.5%, 11%, 11.5%, 12%, 12.5%, 13%, 13.5% or 14% w/w).

In some embodiments, the compositions described herein may further comprise viable probiotic bacterial cells (e.g., *Lactobacillus* species, *Lactobacillus acidophilus*, *Lactobacillus rhamnosus*, and/or *Lactobacillus bifidus*). In some embodiments, the compositions described herein may further comprise viable probiotic bacterial cells selected from *Bifidobacterium animalis*, *Bifidobacterium adolescentis*, *Bifidobacterium bifidum*, *Bifidobacterium breve*, *Bifidobacterium essensis*, *Bifidobacterium infantis*, *Bifidobacterium lactis*, *Bifidobacterium longum*, *Lactobacillus paracasei*, *Lactobacillus acidophilus*, *Lactobacillus delbrueckii* subsp. *bulgaricus*, *Lactobacillus casei*, *Lactobacillus crispatus*, *Lactobacillus johnsonii*, *Lactobacillus lactis*, *Lactobacillus fermentum*, *Lactobacillus plantarum*, *Lactobacillus rhamnosus*, *Lactobacillus reuteri*, *Lactobacillus salivarius*, *Lactobacillus amylovorus*, *Lactobacillus gasseri*, *Lactobacillus pentosaceus*, *Enterococcus faecalis*, *Enterococcus faecium*, *Pediococcus acidilactici*, *Propioniobacterium freundenreichii*, and *Streptococcus thermophilus*. In some embodiments, other probiotic strains may also be included, as long as they are biocompatible with the probiotic mixtures described herein. In some embodiments, the probiotic bacteria may be present at a concentration of at least 0.5%, 1%, 1.5%, 2%, 2.5%, or 3% w/w. In some embodiments, the probiotic bacteria may be present at a concentration of up to 3.5% w/w (e.g., from 0.1%, 0.2%, 0.3%, 0.4%, 0.5%, 0.6%, 0.7%, 0.8%, 0.9%, 1%, 1.5% to 2%, 2.5%, 3%, or 3.5% w/w).

In some embodiments, the compositions described herein may further comprise exfoliating agents at concentrations sufficient to achieve exfoliation when applied topically to a subject's skin for a treatment period. In some embodiments, the exfoliating agents may comprise proteolytic enzymes (e.g., proteases). In some embodiments, the exfoliating agents may comprise proteolytic enzymes such as papain, bromelain, trypsin, and/or chymotrypsin). In some embodiments, the enzymes may be derived from fruit or from other natural sources (either fermented or non-fermented). In some embodiments, the exfoliating agents may comprise fermented or non-fermented fruit (e.g., *papaya* or pineapple) powder (e.g., at 5-10% w/w; such as from between 5%, 5.5%, 6%, or 6.5% to 7%, 7.5%, 8%, 8.5%, 9%, 9.5%, or 10%). In some embodiments, the exfoliating agents may comprise cosmetically or dermatologically suitable organic acids. In some embodiments, the organic acid(s) may be used as a buffer or part of a buffering system. In some embodiments, the organic acids may be present at no more than 1% w/w total organic acids, and/or the organic acids may be a mixture of organic acids, wherein each organic acid is present at 0.02-0.05% w/w. In some embodiments, the exfoliating agents may comprise willow bark extract powder (e.g., at 0.5-2% w/w; such as from 0.5%, 0.6%, 0.7%, 0.8% or 1%, to 1.5%, 1.6%, 1.7%, 1.8%. 1.9% or 3% w/w). In some embodiments, the compositions described herein may include organic acids such as ascorbic acid, sorbic acid, citric acid, glycolic acid, lactic acid and acetic acid, benzoic acid, salicylic acid, phthalic acid, phenolsulphonic acid, succinic acid, or any mixture thereof. In some embodiments, the compositions described herein may include benzoic acid, sorbic acid, succinic acid, citric acid, lactic acid, or any mixture thereof. Without being bound by theory, the enzymes and other exfoliating agents may help the other active ingredients in the topical compositions of the present description to penetrate through the outer layer of dead skin cells and reach the inner living skin cells. For example, the enzymes may help facilitate the dissolving of the keratin and dead cells of the substratum corneum (i.e., exfoliation) and open the dermal upper cortex, allowing the other active ingredients to penetrate deeper and reach the layer of living skin cells.

In some embodiments, the compositions described herein may further comprise mud and/or clay (e.g., mineral-rich mud and/or clay, Dead Sea mud or clay, and/or green clay). In some embodiments, the mud and/or clay may be present at a concentration of 0.01-0.5% w/w (e.g., from 0.01%, 0.02%, 0.03%, 0.04%, 0.05%, 0.06%, 0.07%, 0.08%, 0.09%, 0.1%, 0.15%, 0.2%, 0.25%, to 0.3%, 0.35%, 0.4%, 0.45%, or 0.5% w/w). In some embodiments, the green clay may be present at up to 2% w/w (from 0.05%, 0.1%, 0.15%, 0.2%, 0.25%, 0.3%, 0.35%, or 0.4% to 0.5% w/w).). In some embodiments, the composition may comprise zinc gluconate (e.g., at 1-5% w/w; such as from 1%, 1.5%, 2%, or 2.5% to 3%, 3.5%, 4%, 4.5%, or 5% w/w). Without being bound by theory, the mud and/or clay may help absorb toxins, while mineral-rich mud and/or clay may accelerate natural exfoliation and/or help restore skin's pH balance. The concentration of clay in compositions described herein may be adjusted to control the overall texture of the composition. For example, far facial masks, concentrations of clay above 2% w/w may lead to over-drying and hardness of the mask, precluding the activity of the probiotic microorganisms.

In some embodiments, the compositions described herein may further comprise one or more blood circulation promoting agents (also referred to as hyperemic agents or rubefacients) (e.g., mustard powder or mustard-based compounds/powder, or other known stimulators of blood circulation). In some embodiments the mustard powder or mustard-based compounds/powder may be up to 2% w/w (e.g., 0.1%, 0.2%, 0.3%, 0.4%, 0.5%, 0.6%, 0.7%, 0.8%, 0.9%, or 1%, to 1.5%, 1.6%, 1.7%, 1.8%, 1.9%, or 2% w/w).

In some embodiments, the compositions described herein may further comprise one or more of nutrients such as essential amino acids (e.g., one or more of histidine, isoleucine, leucine, lysine, methionine, phenylalanine, threonine, tryptophan, and valine), chlorophyll, vitamins, minerals, antioxidants, and negative ions. In some embodiments, the compositions described herein may further comprise a prebiotic substance. In some embodiments, the compositions described herein may further comprise algae cells or extracts therefrom (e.g., blue-green algae) (e.g., at 1-5% w/w; such as from 1%, 1.5%, or 2%, to 2.5%, 3%, 3.5%, 4%, 4.5%, or 5% w/w). In some embodiments, the compositions described herein may further comprise *spirulina* or *spirulina* powder (e.g., at 1-5% w/w; such as from 1%, 1.5%, or 2%, to 2.5%, 3%, 3.5%, 4%, 4.5%, or 5% w/w).

In some embodiments, the compositions described herein may further comprise sugars and/or polysaccharides (e.g., at concentrations sufficient to stimulate and/or maintain viability of said viable probiotic yeast and bacteria). In some embodiments, the compositions described herein may further comprise hyaluronan (e.g., hyaluronic acid, or salts of hyaluronic acid, such as sodium hyaluronate) and/or a glycosaminoglycan. In some embodiments, the composition may further comprise glycosaminoglycans (GACs) and/or sodium hyaluronate (e.g., at 0.01-0.5% w/w).

In some embodiments, the composition may further comprise a gelling agent. In some embodiments, the composition may further comprise alginate and/or polyvinylpyrrolidone (PVP) (e.g., at 25-50% w/w; such as from 25%, 30%, or 35%, to 40%, 45%, or 50% w/w). The concentrations of these agents may be varied to control the structure/texture of the compositions. For a composition having the structure/texture of a mask or peel, alginate and PVP concentrations of below 25% may result in a composition that is too liquid, whereas concentrations higher than 50% may result in a composition that hardens too much.

In some embodiments, the composition may further comprise essential oils (e.g., at 1-5% w/w). Without being so limited, concentrations of essential oils lower than 1% w/w may not sufficiently mask potentially undesirable odors of the composition.

In some aspects, the present description also relates to topical compositions which are prepared or formulated as a cream, lotion, serum, gel, liquid, powder, butter, peel, scrub, mask, or concentrate.

In some embodiments, the compositions described herein relate to a skin ointment. As used herein, the term "ointment" refers to any topical composition, usually but not always viscous, comprising one or more active ingredients that are intended applied to the skin of a subject as a treatment for a period of time (as opposed to indefinitely). In some embodiments, the compositions described herein may relate to a skin ointment comprising:
  (a) viable probiotic *Saccharomyces* yeast cells (e.g., at a concentration of at least 5% w/w);
  (b) viable probiotic bacterial cells (e.g., at a concentration of at least 0.5% w/w);
  (c) exfoliating agents (e.g., comprising dermatologically suitable proteolytic enzymes and/or organic acids at concentrations sufficient to achieve exfoliation);
  (d) a hyperemic agent (e.g., at a concentration sufficient to stimulate blood circulation while minimizing dermocaustic effects); and
  (e) nutrients (e.g., comprising prebiotics, sugars, and/or polysaccharides, at concentrations sufficient to stimulate and/or maintain viability of said viable probiotic yeast and bacteria).

In some embodiments, the ointment may be formulated to be suitable as a mask applied to a subject's skin to stimulate skin rejuvenation and/or repair.

In some embodiments, the ointment may be adjusted to a pH of between 6 and 7.5, between 6 and 7, preferably about 6.5 to 7, or most preferably about 7.

In some embodiments, contact of the ointment with a subject's skin for a treatment period causes an increase in the ointment's pH as compared to the same ointment incubated for the same treatment period without contacting the subject's skin (e.g., see Example 13). In some embodiments, such increase in pH may suggest that components of the ointment actively interact or participate with the components of the patient's skin during treatment.

In some embodiments, describe herein is a method for preparing a skin ointment, the method comprising:
  (a) providing a dry composition comprising viable probiotic yeast cells;
  (b) providing a dry composition comprising viable probiotic bacterial cells;
  (c) providing an aqueous phase;
  (d) admixing (a), (b), and (c) to produce the skin ointment as defined in claim 1, wherein any combination of said exfoliating agents, said hyperemic agent, and said nutrients are formulated as dry and/or aqueous phases to improve shelf life.

In some embodiments, the compositions described herein may be entirely formulated as a dry composition which is to be reconstituted and/or mixed with an aqueous phase at the time of treatment. In some embodiments, the composition is to be administered within 1 hour of preparation, preferably between 20 to 40 minutes of preparation.

In some aspects, the present description also relates to biocompatible mixture of probiotics as defined herein, which are to be admixed with the aqueous base mixture.

In some embodiments, the biocompatible mixture of probiotics described herein may be a dry composition (e.g., powder, granules, or flakes), that is to be admixed with the aqueous base mixture as defined herein, preferably just before or at the time of use. In some embodiments, the admixture is to be administered within 1 hour, preferably within 20 to 40 minutes of preparation.

In some embodiments, the composition may comprise a biocompatible mixture of probiotics and an aqueous phase or aqueous base mixture comprising one or more of: exfoliating agents, mud and/or clay, blood circulation promoting agent, and nutrients.

In some aspects, the present description also relates to a method for preparing a composition for skin rejuvenation and/or repair, said method comprising combining the biocompatible mixture of probiotics as defined herein, with the aqueous phase as defined herein. In some embodiments, ingredients of the compositions or ointments described herein that are not amenable to dry formulation (e.g., mud, essential oils, and/or glycosaminoglycans) may be comprised in an aqueous phase or aqueous base mixture.

As used herein the term "biocompatible" in the context of mixtures of probiotics of the present description, refers to combinations of live probiotic microorganisms and other ingredients that, when combined, at least retain their beneficial effect on the host organism (e.g., they are not toxic or otherwise detrimental to one another and/or to the host organism).

In some aspects, the present description also relates to a kit for skin rejuvenation and/or repair. The kit may comprise: (a) the biocompatible mixture of probiotics as defined herein; and (b) the aqueous phase as defined herein. In some embodiments, (a) and (b) may be kept separate and are to be admixed just prior to use.

In some aspects, the present description also relates to a method for improving skin rejuvenation and/or repair, the method comprising: (i) admixing the biocompatible mixture of probiotics as defined herein and the aqueous phase as defined herein; and (ii) topically administering the admixture of (i) to skin. In some embodiments, the admixture is to be administered within 1 hour, preferably between 20 to 40 minutes, to skin. In some embodiments, (i) and (ii) may be repeated until a desired level of skin rejuvenation and/or repair is obtained (e.g., allowing at least 1, 2, 3, 4, 5, 6, 7, 8, 9, 10, 11, 12, 13, or 14 days between treatments).

Without being bound by theory, the different components forming part of the compositions described herein are believed to participate in a concerted action, resulting in the efficacy of the present topical compositions for improving skin rejuvenation and/or repair.

The first concerted action includes the dissolving of the keratin and dead cells of the substratum corneum for example due to the concerted action of enzymes such as papain and bromelain. These enzymes open the dermal upper cortex, allowing a second concerted action to take place.

In a second concerted action, the exfoliation or opening of the upper skin layer enables the capture of toxins to take place, due to the action of the high mineral content clays (e.g., present in the Dead sea mud). Its rich mineral content accelerates natural exfoliation and restores skin's pH balance. Furthermore, the concerted actions of these specific components are accelerated by an increase in blood circulation (e.g., by the action of mustard-based components present in the mixture). A reddish skin tint is visible after a certain time of the application of the mask, including a soft warming effect and even a prickling sensation is perceived.

A third concerted action is provided by the activated probiotics (e.g., probiotic yeast and/or probiotic bacteria), which harmonize and support skin cells and skin bacteria.

The fourth and fifth concerted actions are provided by nutrients/antioxidants and blood circulation promoting agents, respectively.

Upon topical administration of the compositions described herein, a reddish skin tint is often visible after a certain time following the application, including a soft warming effect and even a prickling sensation, resulting from the actions of the active ingredients.

In some aspects, the present description relates to one or more of the following items:

1. A topical composition for skin rejuvenation and/or repair, said composition comprising:
   (a) a biocompatible mixture of probiotics; admixed with
   (b) an aqueous base mixture comprising one or more of: exfoliating agents, mud and/or clay, blood circulation promoting agent, and nutrients.
2. The composition of item 1, wherein said probiotics comprise probiotic bacteria and/or yeast.
3. The composition of item 2, wherein said probiotic bacteria comprises a *Lactobacillus*.
4. The composition of item 3, wherein said probiotic bacteria comprises a *Lactobacillus acidophilus*, *Lactobacillus rhamnosus*, and/or *Lactobacillus bifidus*.
5. The composition of item 2, 3 or 4, wherein said probiotic bacteria are present at a concentration of up to 3.5% w/w.
6. The composition of any one of items 2 to 5, wherein said yeast comprises selenium yeast and/or selenium activated fattened yeast cells.
7. The composition of any one of items 2 to 6, wherein said yeast comprises *Saccharomyces cerevisiae*.
8. The composition of item 2, 3 or 4, wherein said probiotic yeast is present at a concentration of about 5-14% w/w.
9. The composition of any one of items 1 to 8, wherein said exfoliating agents comprise proteolytic enzymes.
10. The composition of item 9, wherein said proteolytic enzymes comprise fruit-derived enzymes.
11. The composition of item 9 or 10, wherein said proteolytic enzymes comprise papain and/or bromelain.
12. The composition of any one of items 1 to 11, wherein said exfoliating agents comprise fermented *papaya* powder.
13. The composition of item 12, wherein said fermented *papaya* powder is present at a concentration of about 5-10% w/w.

14. The composition of any one of items 1 to 13, wherein said exfoliating agents comprise cosmetically or dermatologically suitable organic acids.
15. The composition of item 14, wherein said organic acids are present at no more than 1% w/w total organic acids.
16. The composition of item 14 or 15, wherein said organic acids are a mixture of organic acids, wherein each organic acid is present at 0.02-0.05% w/w.
17. The composition of any one of items 1 to 16, wherein said exfoliating agents comprise willow bark extract powder.
18. The composition of item 17, wherein said willow bark extract powder is present at 0.5-2% w/w.
19. The composition of any one of items 1 to 18, wherein said mud and/or clay comprise mineral-rich mud and/or clay.
20. The composition of any one of items 1 to 19, wherein said mud and/or clay comprise dead sea mud or clay.
21. The composition of item 19 or 20, wherein said mud and/or clay are present at a concentration of 0.01-0.5% w/w.
22. The composition of any one of items 1 to 21, wherein said mud and/or clay comprise green clay.
23. The composition of item 22, wherein said green clay is present at up to 2% w/w.
24. The composition of any one of items 1 to 23, further comprising zinc gluconate.
25. The composition of item 24, wherein said zinc gluconate is present at 1-5% w/w.
26. The composition of any one of items 1 to 25, wherein said blood circulation promoting agent comprises mustard or mustard-based compounds.
27. The composition of item 26, wherein said mustard or mustard-based compounds is up to 2% w/w.
28. The composition of any one of items 1 to 27, wherein said nutrients comprise *spirulina*.
29. The composition of item 28, wherein said *spirulina* is *spirulina* powder and is present at 1-5% w/w.
30. The composition of any one of items 1 to 29, wherein said nutrients comprise one or more of essential and/or semi-essential amino acids, chlorophyll, vitamins, minerals, antioxidants, and negative ions.
31. The composition of any one of items 1 to 30, wherein said composition further comprises glycosaminoglycans (GACs) and/or sodium hyaluronate.
32. The composition of item 31, wherein said glycosaminoglycans (GACs) and/or sodium hyaluronate is/are present at 0.01-0.5% w/w.
33. The composition of any one of items 1 to 32, wherein said composition further comprises alginate and/or polyvinylpyrrolidone (PVP).
34. The composition of item 31, wherein said alginate and/or polyvinylpyrrolidone (PVP) is/are present at 25-50% w/w.
35. The composition of any one of items 1 to 34, wherein said composition further comprises essential oils.
36. The composition of item 31, wherein said essential oils are present at 1-5% w/w.
37. The composition of any one of items 1 to 36, which is formulated in a cream, lotion, serum, gel, liquid, powder, butter, peel, scrub, mask, or concentrate.
38. A biocompatible mixture of probiotics as defined in any one of items 1 to 8, for admixture with the aqueous base mixture as defined in any one of items 1 and 9 to 36 to produce a topical composition for skin rejuvenation and/or repair.
39. The biocompatible mixture of probiotics of item 38, which is a dry composition, powder, granules, or flakes.
40. An aqueous base mixture as defined in any one of items 1 and 9 to 36, for admixture with the biocompatible mixture of probiotics as defined in any one of items 1 to 8 to produce a topical composition for skin rejuvenation and/or repair.
41. A method for preparing a composition for skin rejuvenation and/or repair, said method comprising combining the biocompatible mixture of probiotics as defined in any one of items 1 to 8, with the aqueous base mixture as defined in any one of items 1 and 9 to 36.
42. A kit for skin rejuvenation and/or repair, said kit comprising:
    (a) the biocompatible mixture of probiotics as defined in any one of items 1 to 8; and
    (b) the aqueous base mixture as defined in any one of items 1 and 9 to 36.
43. The kit of item 42, wherein said biocompatible mixture of probiotics in (a) is a dry composition, powder, granules, or flakes.
44. The kit of item 42 or 43, wherein (a) and (b) are to be admixed at the time of use.
45. A method for improving skin rejuvenation and/or repair, said method comprising:
    (i) admixing the biocompatible mixture of probiotics as defined in any one of items 1 to 8, and the aqueous base mixture as defined in any one of items 1 and 9 to 36; and
    (ii) topically administering the admixture of (i) to skin.
46. The method of item 45, wherein the admixture is to be administered within 20 to 40 minutes to skin.
47. The method of item 45 or 46, further comprising repeating (i) and (ii) until a desired level of skin rejuvenation and/or repair is obtained.
48. The composition of any one of items 1 to 37, the biocompatible mixture of probiotics of item 38 or 39, the aqueous base mixture of item 40, the kit of any one of items 42 to 44, the method of item 41 or 45 to 47, wherein said skin rejuvenation and/or repair comprise one or more of anti-acne treatment, anti-skin redness treatment, anti-scar treatment, anti-wrinkle treatment, anti-melasma treatment, anti-rosacea treatment, anti-eye dark circle treatment, anti-eye puffiness treatment, or any combination thereof.

EXAMPLES

Example 1: Evaluation of Topical Microorganism Application on Skin

The effect of the topical application of different viable probiotic microorganisms on human skin was explored in a series of preliminary patient trials. Briefly, viable probiotic unicellular microorganisms were dispersed in aqueous solution (lacking other active ingredients) and topically applied to the skin of human volunteers having a variety of undesirable dermatological conditions such as acne, wrinkles, scars, melasma, rosacea, eye dark circles, and eye puffiness. The microorganism compositions were left on the skin of the human volunteers for generally between 10 and 20 minutes in a single treatment. The results were assessed by a combination of visual inspections by the professional administering the treatment and patient self-reporting, both immediately following the treatment, as well as in subsequent patient follow-up visits up to about 14 days post-treatment.

The microorganisms screened for beneficial skin effects included multiple probiotic bacteria (e.g., lactic acid bacteria including *Lactobacillus bifidus* and *Lactobacillus rhamnosus*), as well as several *Saccharomyces* yeast strains (including *Saccharomyces boulardii*, *Saccharomyces cerevisiae*, and selenium yeast produced by fermenting *Saccharomyces cerevisiae* in a selenium-rich media). However, in each case, the results were either inconsistent from patient to patient, and/or deemed unsatisfactory in terms of the beneficial effects on the skin of the patients as assessed by the treating professional and/or post-treatment feedback from patients.

Example 2: Potentiation of Topical Application of Viable Yeast

In an attempt to potentiate the effects of the topical applications of viable microorganisms, further patient trials were conducted using an ointment prepared with a single viable microorganism culture (*Saccharomyces cerevisiae* yeast; 5-14% w/w of ointment) admixed with an aqueous phase comprising a mixture of dermatologically acceptable ingredients including one or more of exfoliating agents (e.g., organic acids and proteolytic enzymes), a hyperemic agent, a nutrient source (e.g., a mineral-rich mud such as Dead Sea mud), sugars/polysaccharides (e.g., glycosaminoglycans (GACs)/sodium hyaluronate), a dermatologically acceptable clay, and a gelling agent to achieve the desired texture (e.g., a facial mask).

Promising results were obtained in terms of the beneficial effects on the skin of the patients as assessed by the treating professional and/or post-treatment feedback from patients. For example, the skin effects of the ointment described above were evaluated in a trial of 8 patients, each patient having from medium to severe acne. The ointment was applied to each patient as a facial mask for about 20 minutes in a single treatment, and the effects were quantified 15 days post-treatment by patient follow-up visits and assessments performed by the treating professional pertaining to: the amount of sebum produced; number of eruptions; size of eruptions (edema and diameter); and speed of healing of eruptions. Overall, the patients presented an improvement of their symptoms by 15-25%, and generally reported quicker drying and/or healing of their eruptions. Overall percentage improvements, in most cases, was assessed by asking the independent opinions of 4-5 people, including the patient. In some cases, the number of eruptions were counted and the values were considered in the overall assessments. Interestingly, the positive results of the ointment were lost by substituting the viable yeast cells with non-viable yeast extracts. In contrast, replacing the viable yeast cells with viable selenium yeast cells in the ointment resulted in improved performance of the ointment. Accordingly, ointments comprising viable selenium yeast cells were utilized in the subsequent Examples.

Example 3: Effect of Supplementation with Probiotic Bacteria

The ointments of Example 2 were modified by supplementing with viable probiotic bacteria such as lactic acid bacteria (including *Lactobacillus bifidus* and *Lactobacillus rhamnosus*; up to 3.5% w/w of the ointment) and further patient trails were conduced as described in Example 2. Improved results over the ointment of Example 2 were consistently observed, particularly in the speed of healing and reduced future eruptions (in the cases of acne). For example, in a trial of 10 patients having moderate to severe acne (including 4 members of the 8-patient trial described in Example 2), a 30% improvement in terms of patient acne symptoms was observed as compared to the corresponding ointments of Example 2.

Example 4: Effect of Supplementation with Prebiotic Algae

The ointments of Example 3 were modified by further supplementing with algae (e.g., prebiotic algae such as blue-green algae; 1-5% w/w of the ointment) and the further patient trails were conducted as described in Examples 2 and 3. Improved results over the ointments of Examples 2 and 3 were consistently observed, particularly in the speed of healing, reduced future eruptions (in the cases of acne), and reduced redness. Overall, ointments containing a combination of the three microorganisms (yeast, probiotic bacteria, and prebiotic algae) resulted in improved efficacy by more than 50% over corresponding ointments containing only yeast. For example, in a trial of 5 patients having moderate to severe acne, an 85% improvement in terms of patient acne symptoms was observed as compared to the corresponding ointments of Example 2.

Example 5: Hyperemic Agents

During initial patient testing of the ointments, an infrared lamp was used to increase the skin temperature and to create a more favorable environment for the microorganisms. To eliminate this step, the incorporation of a hyperemic agent directly into the ointment was considered. Surprisingly, patient testing revealed that the inclusion of hyperemic agents was found to potentiate the effects of the viable microorganisms in the ointments described in Examples 2-4. Hyperemic agents tested in a plurality of patient trials included essential oils from cinnamon and clove, cayenne pepper powder, chilli oil, as well as those stemming from oils and powders from Brassicaceae mustards. In particular, the inclusion of Brassicaceae mustard seed power in the ointment resulted in increased efficacy of the ointment as compared to other hyperemic agents tested, particularly when used at concentrations of between 0.5% and 2% w/w in the ointment. The use of excessive amounts of hyperemic agent resulted in undesirable hypersensitivity and/or dermocaustic effects (particularly for patients with sensitive skin), while the use of insufficient amounts of hyperemic agent resulted in decreased ointment efficacy.

Example 6: Exfoliating Agents

The inclusion of exfoliating agents (chemical and/or enzymatic) was found to potentiate the effects of the viable microorganisms in the ointments described in Examples 2-4. Exfoliating agents having potentiating effects that were tested included proteolytic enzymes, dermatologically acceptable organic acids, *papaya* powder (both fermented and non-fermented), and willow bark extract powder.

It was found that controlling the final concentrations and/or combinations of organic acids in the ointment had an effect not only on the performance of the ointment, but also on minimizing unwanted patient skin irritations. Including organic acids of different sizes in the ointment (e.g., between 2 and 5 different types of organic acids) allowed the total concentration of organic acids in the ointments to be decreased while maintaining efficacy. In turn, minimizing the total concentration of organic acids in the ointment not only improved patient tolerance and minimized unwanted skin irritations (particularly for patients or areas of sensitive skin), but it also allowed for increasing concentrations of other active ingredients without disrupting the texture of the ointment (e.g., the ointment becoming too liquid). In general, it was found that ointments containing a total organic acid concentration above 1.3% w/w resulted in skin irritation, blistering and/or hypersensitivity in patients with sensitive skin.

Both fermented and non-fermented *papaya* powder were explored as a natural source of proteolytic enzymes (also as a source of nutrients, vitamins, and antioxidants). Improved efficacy of the ointments was observed using fermented *papaya* powder as compared to non-fermented *papaya* powder. Furthermore, the use of fermented *papaya* powder provided the added benefit of leaving a carotenoid-based natural coloring (i.e., natural tanning), which patients ultimately liked and found desirable.

Example 7: Effect of Supplementation with Sugars and Polysaccharides

Interestingly, it was found that the efficacy of the ointments, and more particularly the activity of the viable microorganisms therein, could be increased by supplementing the ointment with sugars and/or polysaccharides. Increased activation of the microorganisms in the ointment was visible by increased bubbling (e.g., carbon dioxide release). Including highly polar polysaccharides having high water-binding capacity (e.g., glycosaminoglycans, hyaluronic acids) was particularly advantageous, as they also served to hydrate the skin.

Example 8: Nutrient Sources

The inclusion of nutrient sources such as mud (e.g., lake or sea mud) rich in trace elements improved the performance of the ointments. Without being bound by theory, it is thought that the nutrient sources work in concert with the other active ingredients in the ointment (e.g., viable microorganisms, exfoliating agents, and hyperemic agents) to nourish the patient's skin, thereby improving the efficacy of the ointment.

Example 9: Clay

The inclusion of a cosmetic clay further improved the performance of the ointments. Without being bound by theory, it is thought that the cosmetic clay (e.g., green clay) works in concert with the other active ingredients in the ointment (e.g., viable microorganisms, exfoliating agents, and hyperemic agents) to adsorb and/or absorb toxins/waste produced during treatment with the ointment. The concentration of clay in the ointment was optimized for the desired texture. For example, for a facial mask, the use of too much clay (e.g., above 2% w/w) resulted in too rapid hardening and drying of the mask, as well as negative effects on the microorganisms and on performance of the treatment.

Example 10: Gelling Agents

The inclusion of gelling agents provided control over the structure/texture to the ointment, depending on what was desired. For example, for a facial mask, a soft and moist texture was found to be particularly desirable, which could be provided by the use of alginate at a concentration of 25-50% w/w, and more preferably between 40-50% w/w. Other gelling agents tested included polyacrylates, xanthan gum, and gelatin.

Example 11: Essential Oils

Several mixing tests with different types and amounts of essential oils were performed to arrive at a mixture that camouflages the unpleasant smell of microorganisms in the ointment, without negatively affecting the performance or side effects of the treatment. The use of both citrus and floral essential oils was explored, and it was found that a mixture of both types of essential oils at concentrations of 0.8-2% w/w was generally sufficient to mask unpleasant odors without causing hypersensitive reactions (e.g., dry or irritated skin).

Example 12: Ointment Formulation for Increased Shelf-Life

As several active ingredients in the ointment (e.g., viable microorganisms, proteolytic enzymes) were not compatible for long-term storage in liquid form, the components of the ointment were formulated into at least two phases: (1) a dry, particulate phase, and (2) one or more liquid phases. The dry particulate phase comprised powdered preparations/formulations of at least the viable microorganisms (yeast, probiotic bacteria, and optionally prebiotic algae) in dormant form. In some formulations, the dry particulate phase also comprised powdered preparations of proteolytic enzymes, organic acids, and/or gelling agents. The other components of the ointment were formulated in one or more liquid phases.

Formulation of components of the ointment into separate dry and wet phases increased the shelf life of the product, allowing the ointment to be prepared just prior to its application on the skin of patients by mixing the solid and liquid phases and thereby activating the dormant microorganisms in "real-time" on the skin of patients.

Example 13: Ointment pH Increases During Treatment

It was found that adjusting or formulating the ointment to a pH below 6 was not well tolerated by patients. In contrast, a pH adjusted too high (over pH 7.5) decreased efficacy of the ointment. Ideally, an ointment pH of about 7 was well tolerated by patients and did not negatively affect efficacy.

Interesting, when the dry phase and liquid phase were mixed (see Example 12) as a control and left alone for 15 minutes without being applied to the skin of patients, the pH of the ointment at the end of the incubation remained at about 7. However, when the dry phase and liquid phase were mixed and the ointment was applied to the skin of patients for 15 minutes, the pH of the ointment increased from about 7 at time zero to pH 7.5 after 15 minutes. These results suggest that components of the ointment actively interact or participate with the components of the patient's skin during treatment.

Example 14: Optimization of Number of Treatments

At the outset of testing, at least two treatments per patient were planned with the idea that a first treatment would be necessary to remove a layer of dead cells, and that a second treatment could then be performed to facilitate the activity/absorption of the active agents with the patient's skin.

Surprisingly, efficacy of the ointment was not increased after two treatments as compared to a single treatment. In fact, there were more incidences of skin irritations and other undesirable side effects when the patent was subjected to two successive treatments.

Example 15: Biocompatible Mask Formulation

Compositions comprising the following commercially available ingredients were prepared and tested for their beneficial effects on skin when applied topically as a biocompatible facial mask. The recited concentrations of each ingredient were empirically determined based on positive effects on skin treated with the compositions.

| Ingredient(s) | Concentration (% w/w) | Phase | Function |
|---|---|---|---|
| Proteolytic enzymes | 1-6% | Dry | Exfoliation or opening of the upper skin layer |
| Fermented papaya powder | 5-10% | Dry | |
| Organic acids | 0.02-0.05% of each organic acid; no more than 1% total organic acids | Dry | |
| Willow bark extract powder | 0.5-2% | Dry | |
| Yeast | 5-14% | Dry | Probiotics |
| *Lactobacillus* | up to 3.5% | Dry | |
| Algae (Spirulina powder) | 1-5% | Dry | Nourishes skin cells. Rich in proteinaceous nutrients and trace elements. |
| Mustard powder | up to 2% | Dry | Creates a "warming" sensation on the skin and increases blood flow/circulation. Toxins are secreted locally and are absorbed by the clay. |
| Green clay | up to 2% | Dry | Absorption of toxins |
| Glycosaminoglycans (GACs) | 0.01-0.5% | Liquid | Polysaccharide having high water-binding capacity that helps regulate intercellular water and maintain skin turgor. Stimulates fibroblasts. |
| Sodium hyaluronate | 0.01-0.5% | Dry | Polysaccharide having high water-binding capacity that helps regulate intercellular water. Helps form a reservoir of water for skin cells. |
| Dead sea mud | 0.01-0.5% | Liquid | Provides the skin with nutrients that |
| Zinc gluconate | 1-5% | Dry | help support enzymatic reactions |
| Alginate | 25-50% | Dry | Gelling agents, providing |
| Polyvinylpyrrolidone (PVP) | | Dry | structure/texture to the composition |
| Essential oils | 0.8-2% | Liquid | Natural perfuming agents |

Concentrations of total organic acids higher than 1% w/w in the compositions were associated with undesirable skin redness. Increasing the relative concentrations of yeast to higher than 14% w/w did not provide improved results on skin, and decreased the relative concentrations of other ingredients in the composition. At concentrations of mustard powder higher than 2% w/w, there was an increased risk of "burning" the skin. Concentrations of green clay higher than 2% w/w resulted in too much drying of the skin.

The concentrations of the gelling agents were varied to control the structure/texture of the compositions. For a composition having the structure/texture of a mask or peel, alginate and PVP concentrations of below 25% resulted in a composition that was too liquid, whereas concentrations higher than 50% resulted in compositions that hardened too much.

As shown in the Table above, some ingredients were formulated in dry (e.g., powder form), while other ingredients were formulated in liquid form. This was done to improve shelf life of the composition, enabling the dry and liquid phases to be combined just prior to a subject being treated.

Example 16: Anti-Wrinkle Treatment with Biocompatible Mask

The biocompatible mask was prepared as described in Example 15 by mixing the powder and liquid phases just prior to application on the skin of subjects. Subjects were subjected to 5 treatments, with 14 days between each treatment, wherein each treatment comprised:
(1) scrubbing with exfoliating bamboo grains and keratolytics;
(2) applying moisturizing serum to soak the skin;
(3) application of the biocompatible mask (topical composition was prepared as described in Example 15) for 20 minutes covered with plastic wrap;
(4) removing the mask applied in step (3); and
(5) applying moisturizer.

Representative results of a treated subject are shown in FIG. 1, which shows pictures of a subject before (FIG. 1A) and after (FIG. 1B) receiving the above treatment.

Example 17: Anti-Scar Treatment

The biocompatible mask was prepared as described in Example 15. Subjects were subjected to 5 treatments, with 14 days between each treatment, wherein each treatment comprised:
(1) scrubbing with exfoliating bamboo grains and keratolytics;
(2) applying moisturizing serum to soak the skin;
(3) application of the biocompatible mask (topical composition was prepared as described in Example 15) for 20 minutes covered with plastic wrap;
(4) removing the mask applied in step (3); and
(5) applying moisturizer.

Representative results of a treated subject are shown in FIG. 2, which shows pictures of a subject before (FIG. 2A) and after (FIG. 2B) receiving the above treatment.

Example 18: Anti-Wrinkle and Scar Treatment

The biocompatible mask was prepared as described in Example 15. Subjects were treated as follows:
(1) scrubbing with exfoliating bamboo grains and keratolytics;
(2) applying moisturizing serum to soak the skin;
(3) application of the biocompatible mask (topical composition was prepared as described in Example 15) for 20 minutes and massaged after 10 minutes;
(4) removing the mask applied in step (3);
(5) applying serum; and
(6) applying moisturizer.

Figure 3B:

Representative results of a treated subject are shown in FIG. 3, which shows pictures of a subject before (FIG. 3A) and after (FIG. 3B) receiving the above treatment.

Example 19: Additional Biocompatible Mask Treatment Results

The biocompatible masks prepared as described in Example 15 were applied to patients having a variety of skin conditions, as generally described in Examples 16-18. Results are shown in FIGS. 4-11.

FIG. 4 shows before (A) and after (B) pictures of a patient treated for facial skin tone after 3 biocompatible mask treatments.

FIG. 5 shows before (A) and after (B) pictures of a patient treated for facial acne after 5 biocompatible mask treatments.

FIG. 6 shows before (A) and after (B) pictures of a patient treated for facial acne after 4 biocompatible mask treatments.

FIG. 7 shows before (A) and after (B) pictures of a patient treated for facial acne after 4 biocompatible mask treatments.

FIG. 8 shows before (A) and after (B) pictures of a patient treated for facial rosacea and melasma after 10 biocompatible mask treatments.

FIG. 9 shows before (A) and after (B) pictures of a patient treated for wrinkles after 1 biocompatible mask treatment.

Figure 10A:
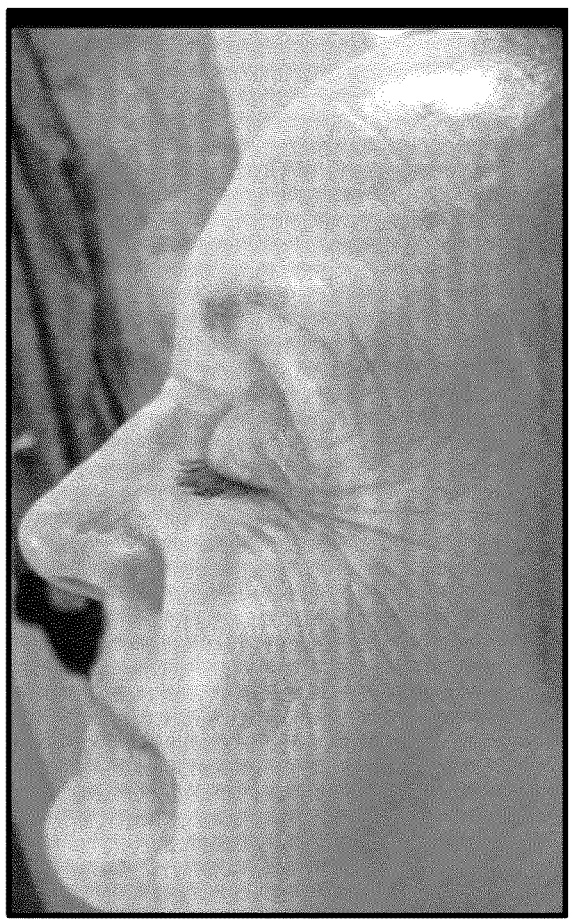
FIG. 10 shows before (A) and after (B) pictures of a patient treated for wrinkles after 4 biocompatible mask treatments. The reduction in the number of wrinkles of the images in FIG. 10 were quantified using custom software.
Figure 10B:
Figure 11A:
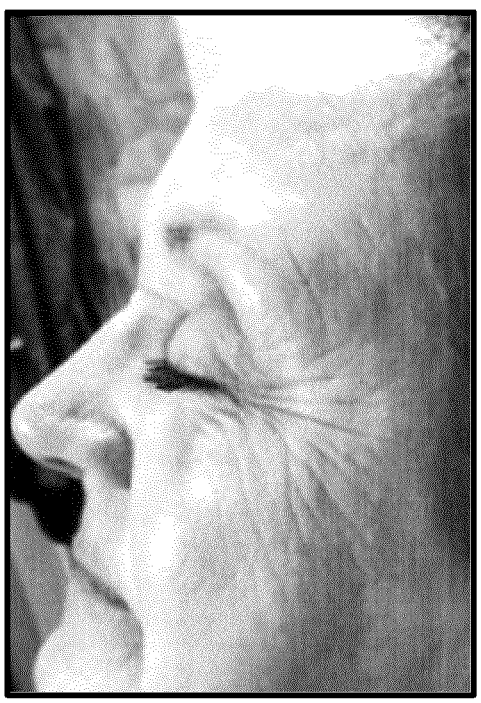
FIG. 11 shows the digital image analysis approach. The approach involved the following steps: capturing high-resolution digital pictures of a patient before and after treatment (FIGS. 11A and 11B); isolating the region of analysis (FIGS. 11C and 11D); transformation into gray tones, 8 bits (FIGS. 11E and 11F); thresholding of the intensity for binarization; counting positive bits; and comparing the count of the two images.
Figure 11B:
Figure 11C:
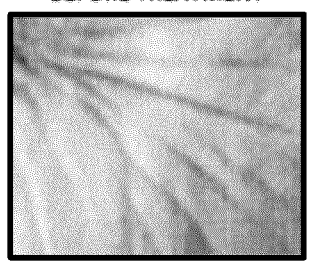
Figure 11D:
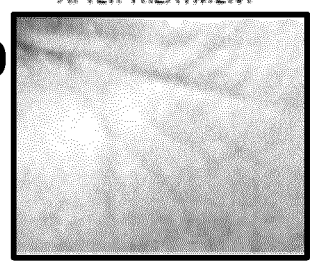
Figure 11E:
Figure 11F:
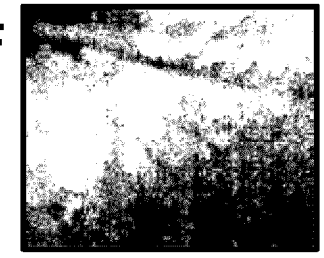

FIG. 10 shows before (A) and after (B) pictures of a patient treated for wrinkles after 4 biocompatible mask treatments. The reduction in the number of wrinkles of the images in FIG. 10 were quantified using custom software developed for the Applicant specifically for such purposes. The custom software employs a digital image analysis approach, as shown in FIG. 11. The approach involved:
1. Capturing high-resolution digital pictures of a patient before and after treatment (FIGS. 11A and 11B);
2. Isolating the region of analysis (FIGS. 11C and 11D);
3. Transformation into gray tones, 8 bits (FIGS. 11E and 11F);
4. Thresholding of the intensity for binarization;
5. Counting positive bits;
6. Comparing the count of the two images.

The quantification approach described above revealed a 25.16% reduction in wrinkles in the region of analysis before and after treatment with the biocompatible mask.

The invention claimed is:

1. A skin rejuvenation and/or repair ointment comprising:
(a) viable probiotic *Saccharomyces* yeast cells;
(b) viable probiotic lactic acid bacterial cells;
(c) exfoliating agents comprising dermatologically suitable proteolytic enzymes and/or organic acids at concentrations sufficient to achieve exfoliation;
(d) a hyperemic agent at a concentration sufficient to stimulate blood circulation while minimizing dermocaustic effects; and
(e) nutrients comprising prebiotics, sugars, and/or polysaccharides, at concentrations sufficient to stimulate and/or maintain viability of said viable probiotic yeast and bacteria;
wherein the ointment stimulates skin rejuvenation and/or repair when applied to a subject's skin.

2. The skin rejuvenation and/or repair ointment of claim 1, wherein contact of the ointment with the subject's skin for a treatment period causes an increase in the ointment's pH as compared to the same ointment incubated for the same treatment period without contacting the subject's skin.

3. The skin rejuvenation and/or repair ointment of claim 1, wherein the viable probiotic *Saccharomyces* yeast cells are at a concentration of at least 5% w/w, and/or the viable probiotic lactic acid bacterial cells are at a concentration of at least 0.5% w/w.

4. The skin rejuvenation and/or repair ointment of claim 1, wherein said viable probiotic *Saccharomyces* yeast cells are at a concentration from 5-14% w/w, and/or said viable probiotic lactic acid bacterial cells are at a concentration of up to 3.5% w/w.

5. The skin rejuvenation and/or repair ointment of claim 1, wherein said viable probiotic *Saccharomyces* yeast cells comprise *Saccharomyces cerevisiae, Saccharomyces boulardii*, selenium yeast, and/or selenium activated fattened yeast cells.

6. The skin rejuvenation and/or repair ointment of claim 1, wherein said viable probiotic lactic acid bacterial cells comprise *Lactobacillus*.

7. The skin rejuvenation and/or repair ointment of claim 1, wherein said viable probiotic lactic acid bacterial cells comprise *Lactobacillus acidophilus, Lactobacillus rhamnosus*, and/or *Lactobacillus bifidus*.

8. The skin rejuvenation and/or repair ointment of claim 1, wherein said exfoliating agents comprise proteolytic enzymes and/or at least one cosmetically or dermatologically suitable organic acid.

9. The skin rejuvenation and/or repair ointment of claim 1, further comprising fermented or non-fermented fruit-derived enzymes, papain, bromelain, fermented or non-fermented *papaya* powder, willow bark extract powder, mud, clay, mineral-rich mud, mineral-rich clay, dead sea mud, dead sea clay, green clay, zinc gluconate, mustard powder, mustard-based compounds, *spirulina, spirulina* powder, blue-green algae cells, one or more of essential amino acids and/or semi-essential amino acids, chlorophyll, vitamins, minerals, antioxidants, negative ions, sugars, polysaccharides, a glycosaminoglycan (GAC), a hyaluronan, a gelling agent, alginate, polyvinylpyrrolidone (PVP), and/or essential oils.

10. The skin rejuvenation and/or repair ointment of claim 9, wherein said fermented or non-fermented *papaya* powder is present at a concentration of 5-10% w/w.

11. The skin rejuvenation and/or repair ointment of claim 8, wherein said organic acid is present at a concentration of no more than 1% w/w.

12. The skin rejuvenation and/or repair ointment of claim 9, wherein said willow bark extract powder is present at a concentration of 0.5-2% w/w.

13. The skin rejuvenation and/or repair ointment of claim 9, wherein said green clay is present at a concentration of up to 2% w/w.

14. The skin rejuvenation and/or repair ointment of claim 9, wherein said zinc gluconate is present at a concentration of 1-5% w/w.

15. The skin rejuvenation and/or repair ointment of claim 9, wherein said mustard powder or mustard-based compounds is/are present at a concentration of up to 2% w/w.

16. The skin rejuvenation and/or repair ointment of claim 9, wherein said *spirulina* or *spirulina* powder is present at a concentration of 1-5% w/w.

17. The skin rejuvenation and/or repair ointment of claim 9, wherein said glycosaminoglycan (GAC) or hyaluronan is present at a concentration of 0.01-0.5% w/w.

18. The skin rejuvenation and/or repair ointment of claim 9, wherein said alginate or polyvinylpyrrolidone (PVP) is present at a concentration of 25-50% w/w.

19. The skin rejuvenation and/or repair ointment of claim 9, wherein said essential oils are present at a concentration of 1-5% w/w.

20. The skin rejuvenation and/or repair ointment of claim 1, which is formulated in a cream, lotion, serum, gel, liquid, powder, butter, peel, scrub, mask, or concentrate.

* * * * *